US007742809B2

(12) United States Patent
Sigg et al.

(10) Patent No.: US 7,742,809 B2
(45) Date of Patent: Jun. 22, 2010

(54) ELECTROPORATION CATHETER WITH SENSING CAPABILITIES

(75) Inventors: Daniel C. Sigg, St. Paul, MN (US); Daisy P. Cross, Minneapolis, MN (US); Jesus W. Casas-Bejar, Brooklyn Park, MN (US); Rodolfo A. Padua, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 1327 days.

(21) Appl. No.: 10/647,522

(22) Filed: Aug. 25, 2003

(65) Prior Publication Data
US 2005/0049542 A1 Mar. 3, 2005

(51) Int. Cl.
A61N 1/30 (2006.01)
(52) U.S. Cl. ...................................................... 604/20
(58) Field of Classification Search .................. 604/20, 604/116, 117, 66, 264, 93.01
See application file for complete search history.

(56) References Cited

U.S. PATENT DOCUMENTS

| 5,087,243 | A | | 2/1992 | Avitall |
| 5,147,332 | A | * | 9/1992 | Moorehead ................ 604/247 |
| 5,389,069 | A | | 2/1995 | Weaver |
| 5,403,311 | A | * | 4/1995 | Abele et al. .................. 606/49 |
| 5,499,971 | A | | 3/1996 | Shapland et al. |
| 5,634,899 | A | | 6/1997 | Shapland et al. |
| 5,807,306 | A | | 9/1998 | Shapland et al. |
| 5,807,395 | A | * | 9/1998 | Mulier et al. ................. 606/41 |
| 5,833,715 | A | * | 11/1998 | Vachon et al. .............. 607/120 |
| 5,865,787 | A | | 2/1999 | Shapland et al. |
| 5,925,066 | A | | 7/1999 | Kroll et al. |
| 6,009,347 | A | | 12/1999 | Hofmann |
| 6,090,619 | A | | 7/2000 | Weissig et al. |
| 6,120,493 | A | | 9/2000 | Hofmann |
| 6,208,893 | B1 | | 3/2001 | Hofmann |
| 6,309,370 | B1 | * | 10/2001 | Haim et al. .................. 604/66 |
| 6,347,247 | B1 | | 2/2002 | Dev et al. |
| 6,361,522 | B1 | | 3/2002 | Scheiner et al. |
| 6,516,223 | B2 | | 2/2003 | Hofmann |
| 6,835,193 | B2 | * | 12/2004 | Epstein et al. .............. 604/507 |
| 2002/0099328 | A1 | | 7/2002 | Scheiner et al. |
| 2002/0183738 | A1 | * | 12/2002 | Chee et al. .................. 606/41 |
| 2003/0074024 | A1 | | 4/2003 | Stokes et al. ................ 607/2 |

FOREIGN PATENT DOCUMENTS

FR 2 365 351 4/1978

OTHER PUBLICATIONS

Krassowska, W., "Effects of Electroporation on Transmembrane Potential Induced by Defibrillation Shocks", *PACE*, vol. 18, Sep. 1995, Part I, pp. 1644-1660.
Tovar, O., et al., "Electroporation and Recovery of Cardiac Cell Membrane with Retangular Voltage Pulses", *The American Physiological Society*, 263:H1128-H1136 (1992).
Harrison, R.L., et al. "Electrophoration-Mediated Gener Transfer in Cardiac Tissue", *FESB Letters*, 435:1-5 (1998).

* cited by examiner

*Primary Examiner*—Nicholas D Lucchesi
*Assistant Examiner*—Christopher D Koharski

(57) ABSTRACT

In general, the invention is directed to techniques for delivering macromolecules to a tissue site via electroporation. Particularly, a catheter detects contact between a distal end of the catheter and a target tissue site via a sensing electrode at the distal end of the catheter. The catheter delivers a fluid containing macromolecules to the tissue site upon detecting contact between the tissue site and the catheter. Concurrently or soon after delivery of the fluid, an electrical stimulus is applied to the tissue site. The electrical stimulus can be applied by the catheter or directly from a power supply, such as an implanted pulse generator. The electrical stimulus causes membranes of cells within the tissue site to destabilize, in turn, forming pores through which the macromolecules migrate into the cells of the tissue site.

22 Claims, 5 Drawing Sheets

ELECTROPORATION CATHETER WITH SENSING CAPABILITIES

TECHNICAL FIELD

The invention relates to delivery of macromolecules to a tissue site and, more particularly, delivery of macromolecules and an enhanced local cell uptake of the macromolecules to a tissue site via electroporation.

BACKGROUND

Electroporation is a technique for facilitating the transfer of macromolecules from an extracellular compartment to an intracellular space. The local delivery of therapeutic agent (macromolecules) in a targeted tissue site, along with the application of an electrical stimulus to the targeted tissue site increases the uptake of the agent by cells near or in the target tissue. Application of the electrical stimulus causes membranes of the cells within the tissue site to destabilize, in turn, forming pores through which the macromolecules migrate into the cells of the tissue site.

Treatment of the tissue site via electroporation advantageously allows localized treatment of the tissue site, thus reducing the damage to surrounding healthy tissue. Further, electroporation allows for delivery of lower dosages of macromolecules to the tissue site, thereby reducing side effects caused by some macromolecules introduced in large dosages. Lastly, electroporation may increase the efficiency by which macromolecules are delivered to the tissue site, e.g., increasing the percentage of cells that take up macromolecules, thereby increasing the therapeutic efficacy of the macromolecules.

SUMMARY

In general, the invention is directed to techniques for providing macromolecules to a tissue site via electroporation. More particularly, a catheter includes at least one electrode to detect contact between a target tissue site and the catheter.

Upon detecting contact between the catheter and the target tissue site, the catheter extends a probe into the tissue site and delivers macromolecules dissolved in a fluid or gel to the tissue site. The probe, for example, is manually extended and retracted into the tissue site via a physician. An electrical stimulus is applied to the tissue site to aid in delivery of the macromolecules into cells of the tissue site.

As will be described, the catheter includes a catheter body that defines an inner lumen to accommodate travel of a probe to the tissue site. The catheter is sized for deployment to the tissue site via a vessel within the patient. In accordance with the invention, the catheter includes at least one electrode on a distal end to detect contact between the distal end of the catheter and the tissue site. In some applications, the tissue site comprises myocardial or other cardiac tissues, and the electrode of the catheter detects a cardiac signal, which indicates contact between the catheter and the cardiac tissue.

Upon detecting contact between the distal end of the catheter and the tissue site, the probe extends from the distal end of the catheter body to contact or penetrate the tissue site. In the case where the tissue site comprises a cardiac tissue site, for example, the probe extends from the distal end of the catheter body upon detecting a cardiac signal such as an electrocardiogram (ECG).

The probe defines a fluid delivery lumen and includes one or more exit ports to allow fluid from a fluid supply to exit the fluid delivery lumen. The exit ports can, for example, comprise pressure responsive valves such as slit valves or sleeve valves. The probe can be constructed of an electrically conductive material or include an electrode to sense contact between the distal end of the fluid catheter body and the tissue site. In this manner, the catheter allows for safe delivery of the fluid to the tissue site without requiring visual control, such as fluoroscopy.

The fluid delivered to the tissue site via the catheter contains at least one type of macromolecule for treatment of abnormalities of the tissue site or to induce a therapeutic effect at the tissue site due to an abnormality at a remote tissue or organ site. Examples of suitable macromolecules include but are not limited to deoxyribo nucleic acid (DNA), ribonucleic acid (RNA), a drug, a gene, a peptide, viral or non-viral vector for delivery of therapeutic genes (DNA) and a protein.

In conjunction with or soon after delivery of the fluid to the tissue site, an electrical stimulus, e.g., a single pulse or series of pulses, is applied to the tissue site. In some embodiments, the catheter applies the electrical stimulus to the tissue site via one or more electrodes. For example, the catheter applies the electrical stimulus between the electrode at the distal end of the catheter and a distal tip of the probe when the probe is made from electrically conductive materials.

Otherwise, the catheter applies the electrical stimulus between the electrode at the distal end of the catheter and an electrode located at the distal tip of the probe when the probe is made from non-conductive materials. In other embodiments, an implanted medical device applies the electrical stimulus to the tissue site. For example, an implanted pacemaker-cardioverter-defibrillator (PCD) may apply the stimulus to the tissue site via a cardiac lead. In either case, the electrical stimulus causes membranes of the cells within the tissue site to destabilize, in turn, forming pores through which the fluid to migrate into the cells of the tissue site.

The tissue site can include cells native to the patient, such as healthy or diseased organ tissue. Alternatively, the tissue site can include foreign cells or organisms such as infectious microorganisms, fungi, parasites or the like. As described, the techniques of the invention may be applied to a cardiac tissue site to treat cardiac-related abnormalities. Other potential tissue sites include organs with cancer, tumors, inflammations or other tissue abnormalities. Example organs include the liver, the pancreas, the kidneys, the gall bladder, the colon, the lung and the like.

In one embodiment, the invention provides a catheter comprising a catheter body that defines an inner lumen, a probe within the inner lumen that delivers fluid to a tissue site of a patient, and at least one electrode coupled to the catheter to detect contact between the catheter and the tissue site.

In another embodiment, the invention provides a method comprising electrically sensing contact between a distal end of a catheter and a tissue site of a patient, delivering a fluid that contains at least one type of macromolecule to the tissue site of the patient via the catheter, and delivering an electrical stimulus to the tissue site of the patient to enhance transfer of the macromolecules of the fluid to the tissue site via electroporation.

In another embodiment, the invention provides a system comprising a fluid supply, a catheter that includes a catheter body that defines an inner lumen, a probe within the inner lumen that delivers fluid from the fluid supply to a tissue site of a patient, and at least one electrode coupled to the catheter to detect contact between the catheter and the tissue site, and a power supply to generate an electrical stimulus that is delivered to the tissue site.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
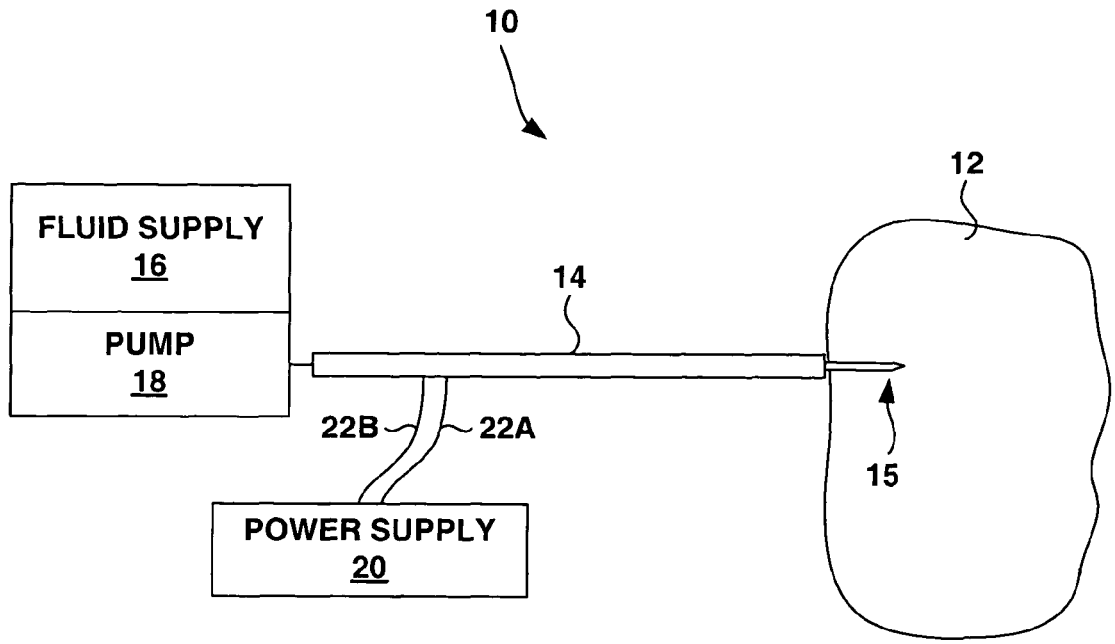
FIG. 1 is a block diagram illustrating an exemplary electroporation system for delivering macromolecules to a tissue site of a patient via electroporation.

FIG. 1 is a block diagram illustrating an exemplary electroporation system 10 for delivering macromolecules to a tissue site 12 of a patient via electroporation. Electroporation is a technique for delivering macromolecules to tissue site 12, or cells within tissue site 12, via application of an electrical stimulus directly to or near tissue site 12.

More specifically, the application of the electrical stimulus causes membranes of the cells within tissue site 12 to destabilize, in turn, forming pores through which the macromolecules migrate into the cells of tissue site 12. Treatment of tissue site 12 via electroporation advantageously allows localized treatment of tissue site 12, thus reducing the damage to surrounding healthy tissue. Further, electroporation allows for delivery of lower dosages of macromolecules to tissue site 12, thereby reducing side effects caused by some macromolecules introduced in large dosages.

Electroporation system 10 includes a catheter 14 that delivers macromolecules dissolved in a fluid or gel as well as an electrical stimulus to tissue site 12 to promote electroporation of the fluid to tissue site 12. Particularly, catheter 14 transports the fluid from a fluid supply 16 to tissue site 12. In some embodiments, electroporation system 10 includes a pump 18 to assist in transporting the fluid of fluid supply 16 through catheter 14. Alternatively, the fluid could be delivered via manual injection, for example, via a syringe. Electroporation system 10 further includes a power supply 20 coupled to catheter 14 via conductors 22A and 22B ("conductors 22"). Power supply 20 generates the electrical stimulus that catheter 14 delivers to tissue site 12.

As will be described in further detail below, catheter 14 defines an inner lumen to accommodate travel of at least one medical component to tissue site 12, such as a probe 15, as well as conductors 22. Catheter 14 can be used to direct probe 15 intraluminally to tissue site 12 via a vessel within the patient. Alternatively, catheter 14 directs probe 15 to tissue site 12 via percutaneous approaches, e.g. via puncture of the skin, or other approaches to deliver macromolecules to internal organs, a tumor in the skin or the like. A portion of probe 15 may be electrically insulated while within the inner lumen in order to reduce the likelihood of oversensing or false sensing due to contact between conductors 22 and probe 15. For example, a portion of probe 15 can be covered with parylene or other suitable material to electrically insulate probe 15.

In accordance with the invention, catheter 14 includes at least one electrode (not shown) on a distal end to detect contact between the distal end of catheter 14 and tissue site 12. In one example, tissue site 12 may comprise myocardial or other cardiac tissues, and the electrodes of the catheter detect a cardiac signal, such as an electrocardiogram (ECG), which indicates contact between the cardiac tissue and the distal end of catheter 14. The ECG signal is visually displayed to a physician via a display. In other embodiments, other variables, such as change in impedance, may be detected to determine contact between the cardiac tissue and the distal end of catheter 14. The physician may be alerted either via a visual or audible signal of the detected contact.

Upon detecting contact between the distal end of catheter 14 and tissue site 12, probe 15 extends from the distal end of catheter 14 to contact or penetrate tissue site 12. Probe 15, for example, is manually extended and retracted into the tissue site via a physician. More specifically, the physician can rotate probe 15 to extend and retract via a screwing motion.

Probe 15 can be constructed of an electrically conductive material or include an electrode to sense contact between the distal end of catheter 14 and tissue site 12. In this manner, catheter 14 allows for safe delivery of the fluid to tissue site 12 without requiring visual control, such as fluoroscopy. Catheter 14 delivers fluid from fluid supply 16 to tissue site 12 via a fluid delivery lumen defined by the probe 15. Probe 15 illustrated in FIG. 1 comprises a needle, however, probe 15 can comprise different configurations, such as a helix-shaped probe.

In conjunction with or immediately following delivery of the macromolecules, catheter 14 applies an electrical stimulus to tissue site 12. Catheter 14 applies the electrical stimulus between the electrode at the distal end of catheter 14, e.g., the electrode that detects contact with tissue site 12, and probe 15 when the probe is made from electrically conductive materials.

Otherwise, catheter 14 applies the electrical stimulus between the electrode at the distal end of catheter 14 and an electrode located at the distal tip of probe 15 when probe 15 is made from non-conductive materials. As described above, the electrical stimulus causes membranes of the cells within tissue site 12 to destabilize, in turn, forming pores through which the fluid to migrate into the cells of tissue site 12.

As described, power supply 20 generates the electrical stimulus for delivery to tissue site 12 via catheter 14. In some embodiments, power supply 20 is an electrical pulse generator that generates voltage pulses for catheter 14 to deliver via electrodes located in close proximity to tissue site 12. Power supply 20 generates a single electrical stimulus, e.g., a single shock to tissue site 12, or a series of electrical stimuli spaced apart at particular time intervals.

Exemplary types of electrical stimuli that are generated by power supply 20 include square waves, triangle waves, sine waves, and exponential decay waves. The electrical stimuli further can be monophasic or biphasic. Some exemplary pulse parameters include pulse amplitude range of 50-900 volts, pulse frequency range from 25-100 kilohertz (kHz), pulse duration range from 1-10 milliseconds (ms), number of sets of stimuli range from 1-5.

In one example, catheter 14 delivers one or more set of stimuli with 5 bursts, each burst having a 300 V amplitude, 1 ms duration, and a frequency of 25 kHz. However, the pulse parameters described above are for exemplary purposes only. The pulse parameters vary significantly depending upon device size, probe length, electrode position, tissue thickness, solutions of macromolecules delivered, and the like.

Fluid supply 16 contains a fluid that includes at least one type of macromolecule dissolved within the fluid for delivery to tissue site 12 for treatment of tissue site 12 or to induce a therapeutic effect at tissue site 12 due to an abnormality at a remote tissue or organ site. Examples of suitable macromolecules include but are not limited to deoxyribo nucleic acid (DNA), ribonucleic acid (RNA), a drug, a gene, a peptide, viral or non-viral vector for delivery of therapeutic genes (DNA) and a protein.

Fluid supply 16 can be located within a body of the patient or outside the body of the patient. In some embodiments, for example, fluid supply 16 is an external fluid supply that couples to a portion of catheter 14 extending from the body of the patient. In other embodiments, fluid supply 16 is an implanted fluid reservoir that couples to catheter 14 to supply catheter 14 with fluid.

Tissue site 12 can include cells native to the patient, such as healthy or diseased organ tissue. Alternatively, tissue site 12 can include foreign cells or organisms such as infectious microorganisms, fungi, parasites, or the like. As described above, the techniques of the invention may be applied to a cardiac tissue site to treat cardiac-related abnormalities. Other potential tissue sites include organs with cancer, tumors, inflammations, or other abnormalities. Example organs include the liver, the pancreas, the kidneys, the gall bladder, the colon, the lung and the like.

Figure 2:
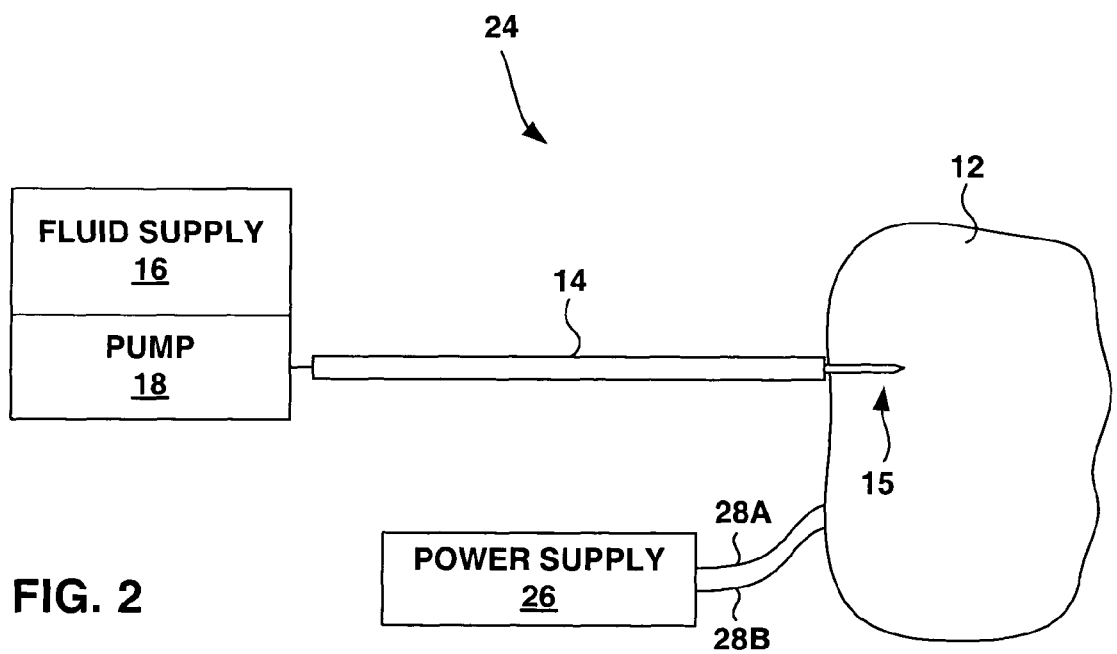
FIG. 2 is a block diagram illustrating another exemplary electroporation system for delivering macromolecules to a tissue site of a patient via electroporation.

FIG. 2 is a block diagram illustrating another exemplary electroporation system 24 for delivering macromolecules to a tissue site 12 of a patient via electroporation. Electroporation system 24 conforms substantially to electroporation system 10 of FIG. 1, but the electrical stimulus for electroporation is applied to tissue site 12 via a power supply 26 instead of via catheter 14. More specifically, power supply 26 delivers the electrical stimulus to tissue site 12 via leads 28A and 28B ("leads 28").

Leads 28 include electrodes located at the distal ends of leads 28, e.g., at the lead-tissue interface, for delivering the electrical stimulus to tissue site 12. In some embodiments, power supply 26 is located within the body of the patient, e.g., power supply 26 comprises an implanted medical device. In other embodiments, power supply 26 is located external to the body of the patient and leads are placed in close proximity to tissue site 12.

In one example, electroporation system 24 is used to deliver macromolecules to cardiac tissue of the patient to treat cardiac-related abnormalities. For instance, power supply 26 comprises an implanted medical device such as a pacemaker/cardioverter/defibrillator (PCD). The PCD includes cardiac leads located in different chambers of the heart.

The cardiac leads have ring and tip electrodes used to deliver an electrical stimulus to the cardiac tissue of the heart during delivery of the macromolecules. In this manner, the PCD is multi-functional, providing pacing, defibrillation, and cardioversion as well as electrical stimuli for electroporation. In another example, catheter 14 could be an implanted cardiac lead.

More specifically, a proximal end of a cardiac lead couples to a fluid supply and the cardiac lead delivers macromolecules dissolved within a fluid or a gel as well as an electrical stimulus to the heart of the patient for electroporation in the surrounding cardiac tissue. Other types of possible implanted medical devices include implanted pulse generators (IPGs), implanted cardioverter/defibrillators (ICDs) and the like.

Figure 3:
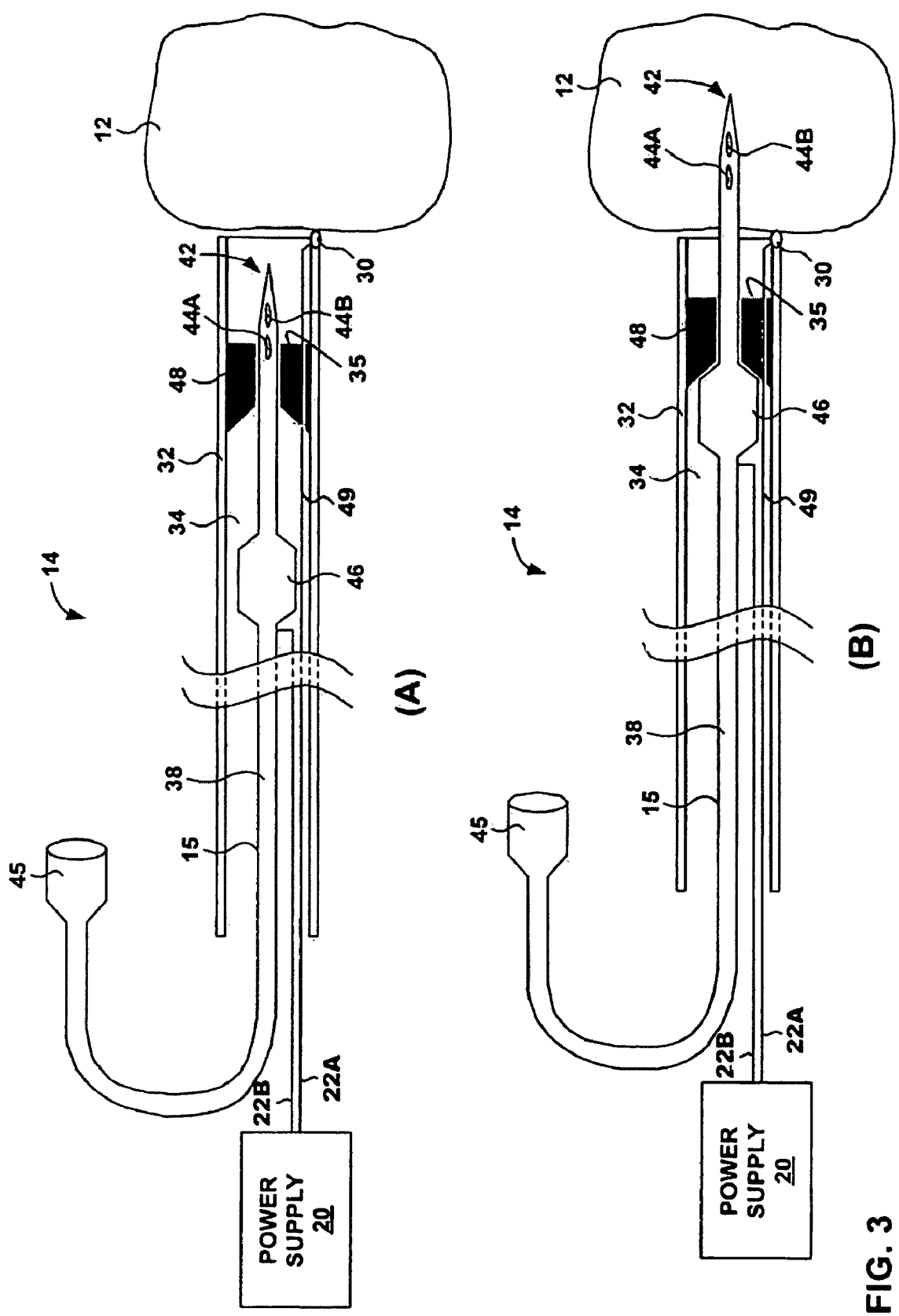
FIG. 3 is a schematic diagram illustrating an exemplary catheter that delivers macromolecules and an electrical stimulus to a tissue site of a patient.

FIG. 3 is a schematic diagram illustrating an exemplary catheter 14 that delivers macromolecules and an electrical stimulus to a tissue site 12 of a patient. In accordance with the invention, catheter 14 includes an electrode 30 to detect contact between catheter 14 and tissue site 12.

As described above, catheter 14 is used for delivering a fluid containing macromolecules and an electrical stimulus to tissue site 12. The electrical stimulus provided to tissue site 12 evokes electroporation to enhance the delivery of the macromolecules to cells within tissue site 12. Catheter 14 includes a catheter body 32 that defines an inner lumen 34 to accommodate travel of a probe 15.

Probe 15, located within catheter body 32, defines a fluid delivery lumen 38 for delivering fluid to tissue site 12. Catheter body 32 directs probe 15 to tissue site 12. Specifically, catheter body 32 is deployed intraluminally to tissue site 12 via a vessel within the patient, thereby directing probe 15 to tissue site 12. Catheter 14 further includes a seal 35 at a distal end of catheter 14 to prevent bodily fluids, e.g., blood, from flowing into catheter body 32.

Electrode 30 of catheter 14 is located at a distal end of catheter body 32 to detect contact between tissue site 12 and the distal end of catheter body 32. In some embodiments, electrode 30 is a sensing electrode that detects contact between tissue site 12 and the distal end of catheter body 32. However, in other embodiments, electrode 30 is a sensing and stimulating electrode.

In this case, electrode 30 may sense contact between tissue site 12 and catheter body 32 as well as be used for delivery of one or more electrical stimuli to tissue site 12. Although catheter 14 of FIG. 3 includes a single electrode 30 located on catheter body 32, catheter body can include more than one electrode on catheter body 32. For example, catheter body 32 may include one electrode for sensing and a second electrode for stimulation.

Probe 15 is coupled to fluid supply 16 (FIG. 1) via a connector interface 45. Connector interface 45 places fluid supply 16 in fluid communication with fluid delivery lumen 38 of probe 15. Connector interface 45 is realized by any of a variety of conventional fluid connection arrangements, e.g., luer lock fittings, ball valve fittings, or the like.

Probe 15 includes a distal tip 42 with exit ports 44A and 44B ("exit ports 44") to allow fluid from fluid supply 16 to exit probe 15 and, more specifically, fluid delivery lumen 38 of probe 15. In some embodiments, exit ports 44 of probe 15 comprise pressure responsive valves, such as slit valves or sleeve valves. For example, exit ports 44 can comprise slit valves formed by cutting one or more slits in a wall of probe 15.

The pressure responsive slit valves open to permit fluid flow through catheter 14 in response to pressure gradients. In another example, exit ports 44 comprise sleeve valves comprising a sleeve that surrounds a portion of a probe 15 proximate each exit port 44, thus covering exit ports 44. The sleeve is constructed of an elastic material to provide the sleeve with the ability to expand and contract in response to pressure gradients, thus opening and closing the sleeve valves. Further, probe 15 may comprise a blunt or sharpened hollow needle similar to an injection needle.

In the example of FIG. 3, exit ports 44 are longitudinally displaced relative to one another. However, in some embodiments, exit ports 44 are circumferentially displaced relative to one another along a length of probe 15. Longitudinally and/or circumferentially displacing exit ports 44 relative to one another prevents structurally weakening distal tip 42 of probe 15 by not placing a multitude of exit ports 44 in a single radial or longitudinal plane.

As illustrated, probe 15 is extendable and retractable. FIG. 3(A) illustrates catheter 14 with probe 15 retracted within catheter body 32 and FIG. 3(B) illustrates catheter 14 with probe 15 extended from catheter body 32 to deliver fluid to tissue site 12. In particular, probe 15 includes a protruded portion 46 that mates with a mechanical stopper 48 to restrict further extension of probe 15 from the distal end of catheter body 32.

For example, a physician can manually extend probe 15 until mechanical stopper 48 mates with and stops protruded portion 46 of probe 15 by rotating probe 15. More specifically, catheter body 32 can include inward extending flanges (not shown) along the inner wall of catheter 14, which mate with grooves (not shown) along an outer body of probe 15.

The flanges and grooves mate such that as the physician rotates probe 15, probe 15 begins to extend from the distal end of catheter 14. In other embodiments, the portion of mechanical stopper 48 through which probe 15 extends may include inward extending flanges that mate with the grooves of probe 15. Probe 15 further retracts within catheter body 32. The extendable and retractable probe 15 allows catheter body 32 to more easily maneuver through the body of the patient to tissue site 12.

Depending on the location of tissue site 12, distal tip 42 of probe 15 may need to protrude different distances from the distal end of catheter body 32. For this reason, catheters for different applications can be configured such that mechanical stopper 48 or protruded portion 46 are located in a particular location to enable a desired penetration depth. In some embodiments, mechanical stopper 48 may form the seal 35 to prevent fluid flow into catheter body 32.

All or a portion of probe 15 is constructed of an electrically conductive material. For example, the distal end of probe 15, including protruding portion 46 as well as distal tip 42, could be constructed of a conductive material. Examples of electrically conductive material used to form probe 15 include stainless steel, platinum, nickel, copper and the like. Distal tip 42 of probe 15, when constructed of a conductive material may sense contact between tissue site 12 and probe 15.

Catheter 14 delivers an electrical stimulus, generated by power supply 20 (FIG. 1), to tissue site 12 via distal tip 42 of probe 15 and electrode 30. Specifically, a conductor 49, which may coils along an inner wall of catheter body 32, electrically couples to electrode 30 to allow catheter 14 to deliver the electrical stimulus generated by power supply 20 to tissue site 12. In some embodiments, catheter 14 includes a connector interface (not shown) that couples conductor 49 to conductor 22A of power supply 20 to conductively couple the electrode 30 to the respective terminal of power supply 20.

In other embodiments, catheter 14 conductively couples to more than one conductor of power supply 20 to conductive components of catheter 14. For example, catheter 14 may conductively couple a first conductor 22A to electrode 30 via conductor 49 and a second conductor 22B to probe 15. As described above, catheter 14 can include insulation (not shown) to insulate a all or a portion of probe 15 within inner lumen 34 to reduce oversensing and false sensing due to contact or electrical interference between probe 15 and electrode 30.

In one embodiment, catheter 14 delivers a series of pulses to tissue site 12 via distal tip 42 of probe 15 and electrode 30. As described above, the application of the electrical stimulus, e.g., the series of pulses, causes membranes of the cells within tissue site 12 to destabilize, in turn, forming pores through which the macromolecules contained in the fluid migrate into the cells of tissue site 12.

In other words, the application of the electrical stimulus via the conductive probe 15 and electrode 30 allows the macromolecules to enter the cells of tissue site 12 via electroporation. Although in the example of FIG. 3 catheter 14 delivers the electrical stimulation to tissue site 12, in other embodiments, power supply 20 delivers the electrical stimulation to tissue site 12 as described in reference to FIG. 2.

Although at least a portion of probe 15 in the example of FIG. 3 is described as being conductive, in other embodiments probe 15 comprises a non-conductive distal tip. The non-conductive distal tip of probe 15 includes an electrode, such as ring electrode, and the catheter delivers an electrical stimulus to tissue site 12 via the ring electrode and electrode 30. In yet another embodiment, the non-conductive distal tip of probe 15 may include multiple electrodes, and the catheter delivers the electrical stimulus via the electrodes of the non-conductive distal tip of probe 15, similar to ring and tip electrodes of a pacing lead.

Figure 4:
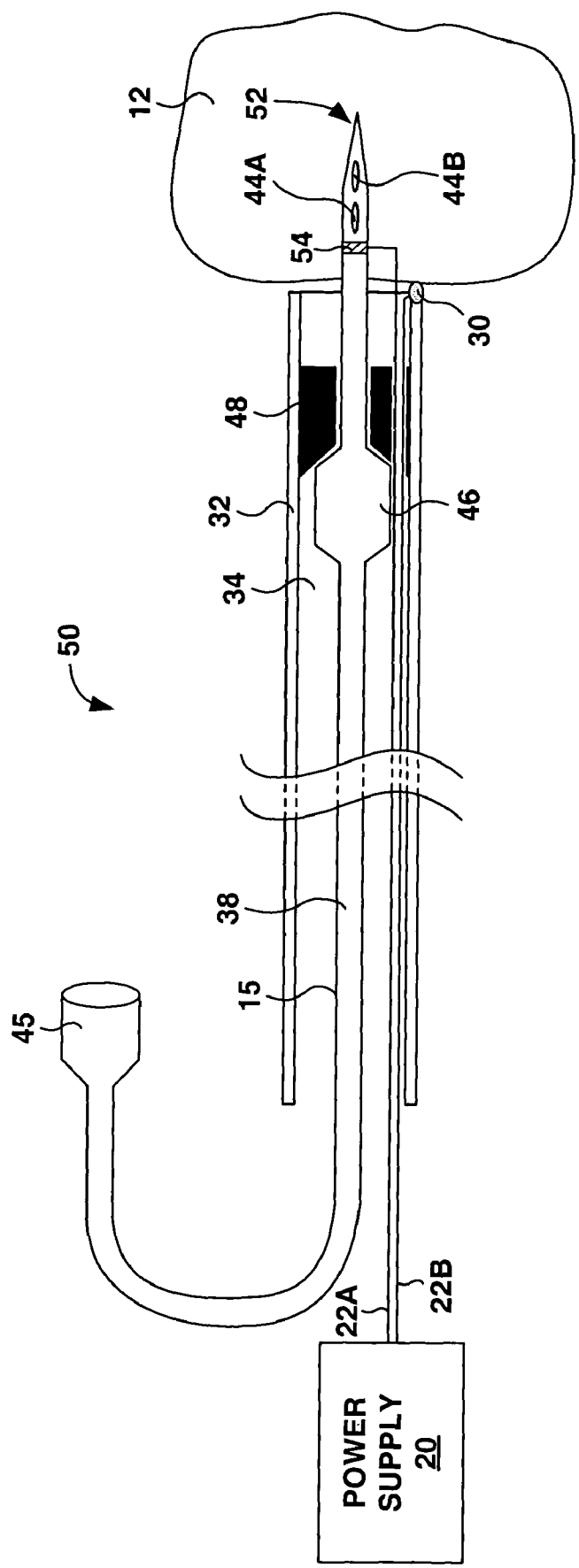
FIG. 4 is a schematic diagram illustrating another exemplary embodiment of a catheter that delivers macromolecules and an electrical stimulus to a tissue site of a patient.

FIG. 4 is a schematic diagram illustrating another exemplary embodiment of a catheter 50 that delivers macromolecules and an electrical stimulus to a tissue site 12 of a patient. Catheter 50 conforms substantially to catheter 14 of FIG. 3, but the distal end of probe 15 has a helix-shaped distal tip 52. Helix-shaped distal tip 52 of probe 15 manually screws into tissue site 12 to anchor probe 15 to tissue site 12.

Helix-shaped distal tip 52 of probe 15 is constructed of an electrically conductive material and couples to a terminal of power supply 20 (FIG. 1) to act as an electrode for delivery of the electrical stimulus. Alternatively, in some embodiments, helix-shaped distal tip 52 of probe 15 is constructed of a non-conductive material and includes one or more electrodes, e.g., ring electrodes and/or tip electrodes, that couple to power supply 20 for delivery of an electrical stimulus.

Figure 5:
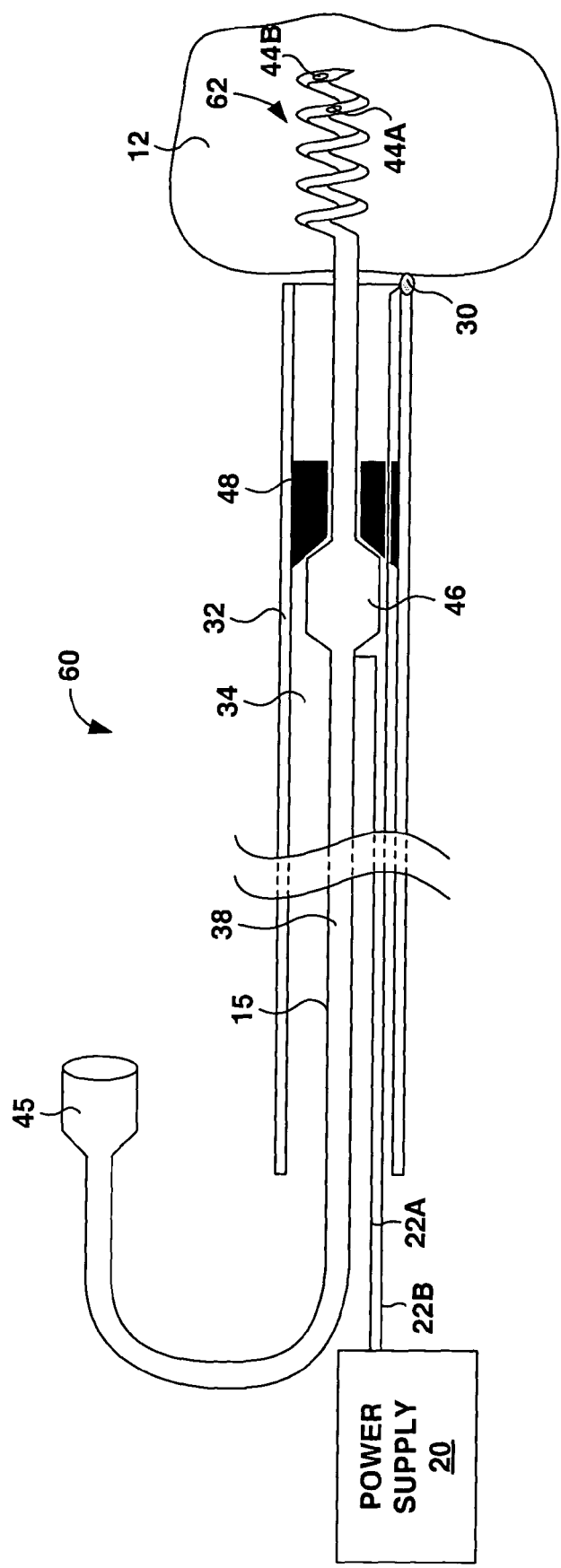
FIG. 5 is a schematic diagram illustrating another exemplary embodiment of a catheter that delivers macromolecules and an electrical stimulus to a tissue site of a patient.

FIG. 5 is a schematic diagram illustrating another exemplary embodiment of a catheter 56 that delivers macromolecules and an electrical stimulus to a tissue site 12 of a patient. Catheter 56 conforms substantially to catheter 14 of FIG. 3, but probe 15 of catheter 56 does not include an electrode 30 at the distal end of catheter 56. Instead, catheter 56 includes a needle tip 58 as well as a helix shaped distal tip 60. Either needle tip 58 or helix shaped distal tip 60 acts as a sensing electrode.

For example, helix shape distal tip 60 senses contact between catheter 56 and tissue site 12. Upon detecting contact between catheter 56 and tissue site 12, a physician may rotate catheter 56 to extend helix shaped distal tip 60 into tissue site 12. In this manner, the physician anchors catheter 56 to tissue site 12. Additionally, the physician also extends needle tip 58 into tissue site 12. Catheter 56 delivers a fluid that contains at least one macromolecule to tissue site 12 via needle tip 58. In addition, catheter 56 delivers electrical stimuli to tissue site 12 via needle tip 58 and helix shaped distal tip 60.

Figure 6:
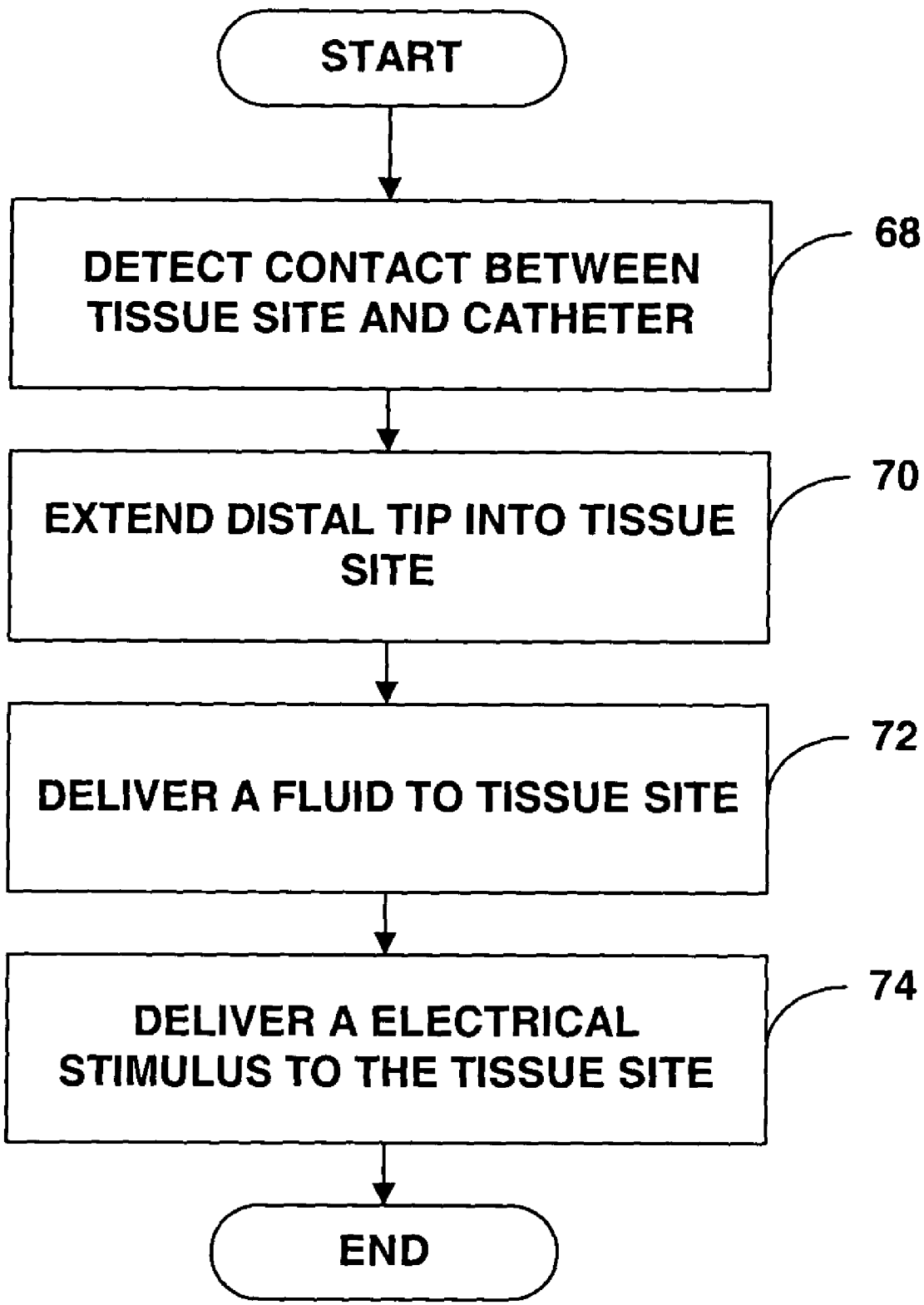
FIG. 6 is a flow diagram illustrating exemplary operation of an electroporation system to deliver macromolecules to a tissue site of a patient via electroporation.

FIG. 6 is a flow diagram illustrating exemplary operation of an electroporation system to deliver macromolecules to a tissue site of a patient. Initially, an electrode of catheter 14 detects contact between catheter 14 and tissue site 12 (68). In one embodiment, catheter 14 includes an electrode located on a distal end of catheter 14 that detects contact between a distal end of catheter 14 and tissue site 12. More specifically, the electrode on the distal end of catheter 14 can be located on a catheter body 32 of catheter 14 or a distal tip of a probe 15, as described above, to provide unipolar sensing.

Alternatively, catheter 14 can include electrodes on both catheter body 32 and the distal tip of probe 15 to provide bipolar sensing between the two electrodes. In another embodiment, the distal tip of probe 15 is made of a conductive material, thus acting as an electrode. When using the techniques of the invention to treat cardiac-related abnormalities, for example, the unipolar or bipolar electrode configuration of catheter 14 detect a cardiac signal, such as an ECG, indicating contact between catheter 14 and a cardiac tissue site. The cardiac signal can be visually displayed to a physician via a display.

Catheter 14 extends probe 15 to contact or penetrate tissue site 12 upon detecting contact between the distal end of catheter 14 and tissue site 12 (70). Catheter 14 and, more particular, a mechanical stop 48 allows probe 15 to extend a particular distance from the distal end of catheter 14. Particularly, mechanical stop 48 mates with a protruded portion 46 of probe 15 to stop probe 15 from extending further into tissue site 12.

Catheter 14 delivers fluid from a fluid supply 16 to tissue site 12 via probe 15 (72). More particularly, probe 15 delivers fluid via one or more exit ports 44 formed near the distal tip of probe 15. As described above, the exit ports 44 can comprise pressure responsive valves such as slit valves or sleeve valves.

Concurrently or soon after delivery of fluid to tissue site 12, an electrical stimulus is applied to tissue site 12 (74). In some embodiments, a power supply applies the electrical stimulus to tissue site 12. For example, the power supply may comprise an implanted PCD that applies a voltage pulse or series of voltage pulses to tissue site 12 via one or more cardiac leads. In other embodiments, catheter 14 delivers the electrical stimulus to tissue site 12.

As described above, catheter 14 applies the electrical stimulus via one of the electrode configurations described. For example, catheter 14 applies a voltage pulse or series of voltage pulses to tissue site 12 via a conductive distal tip of probe 15 and an electrode located at a distal end of catheter body 32. The electrical stimulus causes membranes of the cells within tissue site 12 to destabilize, in turn, forming pores through which the macromolecules migrate into the cells of tissue site 12.

Various embodiments of the invention have been described. For example, in some situations, catheter 14 may be implanted within the body of the patient. These and other embodiments are within the scope of the following claims.

The invention claimed is:

1. A catheter comprising:
a catheter body that defines an inner lumen;
a probe within the inner lumen that delivers fluid to a tissue site of a patient;
a seal within the inner lumen and located at a distal end of the catheter body;
a single point electrode located on the catheter body at a distal end of the catheter body and coupled to the catheter to detect contact between the catheter and the tissue site; and
an electrical stimulus to the tissue site is delivered through the single point electrode and the probe,
the probe comprising a protruded portion that mates with the seal to prevent fluid flow into the catheter body and restrict extension of the probe from the distal end of the catheter body.

2. The catheter of claim 1, wherein the catheter body directs the probe to the tissue site.

3. The catheter of claim 1, wherein the probe comprises an extendable probe that extends from the catheter body upon the electrode detecting contact between the catheter and the tissue site.

4. The catheter of claim 3, wherein the probe comprises an extendable and retractable probe.

5. The catheter of claim 1, wherein the probe includes a distal tip with at least one exit port to allow fluid to exit the probe.

6. The catheter of claim 5, wherein the distal tip of the probe is formed from an electrically conductive material.

7. The catheter of claim 5, wherein the distal tip of the probe comprises a needle.

8. The catheter of claim 5, wherein the electrode is coupled to a distal end of the probe to detect contact between the catheter and the tissue site.

9. The catheter of claim 5 wherein the probe comprising at least two exit ports displaced longitudinally relative to one another along a length of the probe, the exit ports being pressure responsive valves.

10. The catheter of claim 1, further comprising a connector interface to couple the catheter to a fluid supply.

11. The catheter of claim 1, further comprising a connecter interface to couple the catheter to a power supply.

12. The catheter of claim 1, wherein the power supply comprises a cardiac pacing device and the catheter is coupled to the cardiac pacing device to deliver cardiac pacing pulses via the electrode.

13. The catheter of claim 1, wherein the fluid delivered to the tissue site contains at least one type of macromolecule.

14. The catheter of claim 13, wherein the macromolecule includes one of deoxyribo nucleic acid (DNA), ribonucleic acid (RNA), a drug, a gene, a peptide, viral or non-viral vector encoding therapeutic genes (DNA) and a protein.

15. The catheter of claim 1, wherein the tissue site of the patient comprises a cardiac tissue site, and the electrode coupled to the catheter detects a cardiac signal indicating contact between the catheter and the tissue site.

16. The catheter of claim 1 wherein the electrical stimulus delivered during one of a period of fluid delivery and a period after fluid delivery.

17. The catheter of claim 1 wherein the seal comprises a proximally-facing mechanical stopping surface, the protruding portion of the probe mating with the proximally-facing mechanical stopping surface to prevent fluid flow into the catheter body.

18. The catheter of claim 17 wherein the proximally-facing mechanical stopping surface being an angled surface.

19. The catheter of claim 1 wherein the seal comprises an inward extending flange and the probe includes a groove for mating with the inward extending flange, the flange and groove configured to cause extension of the probe from the distal end of the catheter upon rotation of the probe.

20. A catheter comprising:
a catheter body that defines an inner lumen;
a probe within the inner lumen that delivers fluid to a tissue site of a patient;
a seal within the inner lumen and located at a distal end of the catheter body;
a single point electrode located on the catheter body at a distal end of the catheter body and coupled to the catheter; and
an electrical stimulus to a tissue site between the single point electrode and a distal tip of the probe,
the probe comprising a protruded portion that mates with the seal to prevent fluid flow into the catheter body and restrict extension of the probe from the distal end of the catheter body.

21. A catheter comprising:
a catheter body that defines an inner lumen;
a probe within the inner lumen that delivers macromolecules to a tissue site of a patient;

a seal within the inner lumen and located at a distal end of the catheter body;

a first electrode located on the catheter body at a distal end of the catheter body and coupled to the catheter; and an electrical stimulus to a tissue site between the single point electrode and a distal tip of the probe, the probe comprising a protruded portion that mates with the seal to prevent fluid flow into the catheter body and restrict extension of the probe from the distal end of the catheter body.

22. A catheter comprising:

a catheter body that defines an inner lumen;

a probe within the inner lumen that delivers a gene to a tissue site of a patient;

a seal within the inner lumen and located at a distal end of the catheter body;

a single point electrode located on the catheter body at a distal end of the catheter body and coupled to the catheter; and an electrical stimulus to a tissue site between the single point electrode and a distal tip of the probe, the probe comprising a protruded portion that mates with the seal to prevent fluid flow into the catheter body and restrict extension of the probe from the distal end of the catheter body.

\* \* \* \* \*